United States Patent [19]

Woolley

[11] Patent Number: 5,192,406
[45] Date of Patent: Mar. 9, 1993

[54] DEACTIVATED CAPILLARY COLUMNS FOR USE IN CAPILLARY ELECTROPHORESIS

[75] Inventor: Cole L. Woolley, Centre Hall, Pa.

[73] Assignee: Supelco, Bellefonte, Pa.

[21] Appl. No.: 638,934

[22] Filed: Jan. 9, 1991

[51] Int. Cl.$^5$ .................. G01N 27/26; G01N 27/447; B01D 57/02
[52] U.S. Cl. ............................. 204/180.1; 264/299 R
[58] Field of Search .............. 204/182.8, 299 R, 180.1

[56] References Cited

U.S. PATENT DOCUMENTS

| 4,680,201 | 7/1987 | Hjerten | 427/230 |
| 4,994,165 | 2/1991 | Lee | 204/180.1 |

FOREIGN PATENT DOCUMENTS

| 354984 | 2/1990 | European Pat. Off. |
| 8912225 | 12/1989 | PCT Int'l Appl. |

OTHER PUBLICATIONS

*Schomburg*, Influence of Polymer Coating of Capillary Surfaces on Migration Behavior in Micellar Electrokinetic Capillary Chromatography, J. High Res. Chrom. 13, pp. 145-147 (1990).
*Payne*, Simultaneous Deactivation & Coating of Porous Silica Particles for Microcolumn Supercritical Fluid Chromatography, Anal. Chem., vol. 62, p. 1379 (1990).
Jorgenson/Analytical Chem., vol. 53, pp. 1298-1302.
J. Chrom., vol. 218, p. 209, 1981.
Terabe (Anal. Chem., vol. 57, pp. 834-841 (1985) & vol. 56, pp. 111-113 (1984).
Jorgenson/Science, vol. 222, p. 266 (1983).
J. Chrom., vol. 347 pp. 191-198 (1985).
McCormick/Anal. Chem., vol. 60, pp. 2322-2328.
Poppe/J. Chrom., vol. 471, pp. 429-436 (1989).
Bruin/J. Chrom., vol. 480, pp. 339-349 (1989).
Regnier/J. Chrom., vol. 516, pp. 69-78 (1990).
Sepaniak/Anal. Chem., col. 59, pp. 1466-1470 (1987).
Yeung/Anal. Chem., vol. 62, pp. 2178-2182 (1990).
Tsuda/J. Chrom., vol. 248, pp. 241-247 (1982).
Lee/Anal. Chem., vol. 62, p. 1379 (1990).
Noll/Chemistry & Technology of Silicones, 2nd Edition (1986).

*Primary Examiner*—John Niebling
*Assistant Examiner*—John S. Starsiak, Jr.
*Attorney, Agent, or Firm*—John E. Taylor, III

[57] ABSTRACT

The walls of fused-silica capillary columns used for capillary zone electrophoresis and micellar electrokinetic capillary chromatography may be deactivated with polysiloxanes, polysilazanes and other silicone polymers to permit more effective separations without eliminating electro-osmotic flow within the columns.

13 Claims, No Drawings

DEACTIVATED CAPILLARY COLUMNS FOR USE IN CAPILLARY ELECTROPHORESIS

This invention relates to capillary zone electrophoresis, and more particularly to fused silica capillary columns having their walls deactivated to render them more suitable for capillary zone electrophoresis.

BACKGROUND OF THE INVENTION

Capillary electrophoresis or capillary zone electrophoresis, also referred to herein as CZE, is a relatively new entrant to the field of separation technologies. It shows great promise in several areas, especially in the biological chemicals arena. CZE is related to conventional electrophoresis, but shows much higher resolving ability, and much smaller sample sizes can be used. CZE separations involve introducing a buffered solution of analytes into a small-bore capillary column which is typically made of fused silica. A high-voltage differential is then established from one end of the column to the other. The surface silanol groups, because of their low pKa, are largely found in the Si—O— form when the pH is greater than 2. The buffered solution flows with what is termed "electro-osmotic flow", because positive ions align with the negative Si—O— groups, and are attracted to the ground end of the voltage differential. This flow sweeps the dissolved analytes along with it, each at a rate depending upon the analyte's charge-to-mass ratio. This charge-related flow of the analytes is termed the "electrophoretic mobility" of the analytes. Positively charged materials flow in the same direction as the electro-osmotic flow, but more slowly, neutrally charged molecules migrate at the same velocity and in the same direction as the electro-osmotic flow, and negatively charged materials tend to flow through the solution in the direction opposite the electro-osmotic flow. The electro-osmotic flow is frequently strong enough, however, that the net movement of negatively charged materials in the column is also in the same direction as the electro-osmotic flow. As a result, detectors may need to be placed at the end of the column opposite where simple charge flow would predict the analytes to elute. Overall separation is determined by the relative electrophoretic mobilities of the individual analytes. These mobilities can be varied by changes in the charge of the species, usually as a result of pH adjustment. The method is ascribed to J. Jorgenson and the initial publications are *Analytical Chem.*, vol. 53, pp. 1298-1302 and *J. Chrom.*, vol. 218, p. 209, both from 1981. The key discovery was that, by reducing the cross-sectional area of the column through use of microcapillary columns, the current density within the column could be reduced, thereby reducing the heating of the sample, which causes several problems.

Neutral analytes can also be separated by a variation of CZE termed micellar electrokinetic capillary chromatography, also referred to herein as MECC. In this technique a surfactant, usually sodium dodecyl sulfate, is added to the solution of the neutral analytes. As the sodium dodecyl sulfate is negatively charged, it moves in the opposite direction to the electro-osmotic flow. Neutral analytes are swept along with the electro-osmotic flow and are separated based on their partitioning between the surfactant and the surrounding aqueous phase. This technique was introduced by Terabe (*Anal. Chem.* vol.57, pp. 834-841 (1985) and vol. 56, pp. 111-113, (1984)).

The CZE and MECC techniques show promise for the separation of macromolecules of biological interest, including proteins and DNA fragments. The use for proteins is severly limited, however, as they tend to be adsorbed strongly upon the silica surface, which causes broadening of eluting analyte peaks, or even the loss of an entire analyte. This problem was discussed by Jorgenson in *Science*, vol. 222, p. 266 (1983).

Several attacks upon this problem of analyte adsorption onto the silica have been tried in CZE separations. These have involved changes in the mobile phase and coatings for the columns. The strengths and, more importantly, the weaknesses, of each are outlined below.

Changes in the mobile phase have included using phases of high and low pH or high ionic strength, and including organic modifiers in the phase. All of these techniques work to some extent, but they introduce other problems. As the primary interaction between a protein analyte and the surface is a charge interaction between the positive sites on the protein and the negatively charged surface, the pH changes either eliminate the positive charge on the protein (at high pH) or reduce the negative charge on the surface (at low pH). Unfortunately, either condition may denature the protein. Organic modifiers work by further solubilizing the protein, but conditions must be carefully chosen to avoid desolubilizing the protein. The organic modifiers may also denature the protein. Using a mobile phase of high ionic strength works by swamping the solution with buffer cations; this blocks protein interactions with the surface by shielding it with cations. The problem here is that it also makes the liquid much more conductive, which increases current flow and thus increases the heat generated. This heating will degrade resolution, and may even boil the mobile phase, precluding the separation altogether.

Another approach to the problem is to coat the walls of the silica column with an inert coating. Several such coatings have been tried.

Hjerten in U.S. Pat. No. 4,680,201 and *J. Chrom.* vol. 347 pp. 191-198 (1985) reacted the glass column walls with $CH_2=CHCO_2CH_2CH_2CH_2Si(OMe)_3$, then copolymerized this with acrylamide, and also coated the column walls with methylcellulose and crosslinked this coating with formaldehyde. Both of these coatings were intended to eliminate electro-osmotic flow. This prevent both CZE and MECC separations, as both depend upon the electro-osmotic flow for separating analytes. Additionally, the published results indicated that interactions were still occurring.

Similarly, McCormick reported, in *Anal. Chem.* vol. 60, pp. 2322-2328, a poly(vinylpyrrolidinone) coating; his examples utilized low pH and relatively high ionic strength, which introduce the problems of heating and protein denaturing described above.

Poppe, as disclosed in *J. Chrom.* vol. 471, pp. 429-436 (1989), reacted the glass column walls with $(MeO)_3Si(CH_2)_3OCH_2$-epoxide followed by a reaction with poly(ethylene glycol). He found these to be unsuitable for use above pH 5, which severly limits the utility of separations using such coated columns. Schomburg, in *J. High Res. Chrom.* 13, pp. 145-147 (1990), reported a crosslinked poly(ethylene glycol) for use in MECC, but only small-molecule separations were disclosed; its suitability for protein separation was not demonstrated, and details of the column preparation were not disclosed.

Maltose and epoxydiol have also been reported as column coatings by Bruin in *J. Chrom.*, vol. 480, pp.

339–349, (1989). The epoxydiol coating gave poorer results than the poly(ethylene glycol)-coated columns described above, and also operated over a very limited pH range of 3 to 5. The maltose column operated over a wider pH range, but with relatively poor efficiency, and produced poorly shaped peaks.

A polyethyleneimine column has also been reported by Regnier in *J. Chrom.*, vol. 516, pp. 69–78 (1990). This column was prepared by coating the surface with polyethyleneimine and then crosslinking the polyimine with a diepoxide. This coating reduced the dependence of the electro-osmotic flow on the mobile-phase pH; it also tended to reverse the direction of the flow. This was, however, a simple, mechanical coating which was not bonded to the surface. The life of such a non-bonded coating tends to be significantly shorter than that of a bonded coating.

Swedberg disclosed coatings made from $(MeO)_3Si(CH_2)_3NH_2$ in European Patent Publication No. 354 984 and PCT International Publication No. WO 89/12225. This material was first reacted with the glass column wall. The European patent discloses use of the material either as-is, or following reaction with glutaraldehyde and subsequently with a protein, dipeptide, or "other amphoteric compound". This yields a layer in which the electro-osmotic flow can be controlled by pH. The International Application discloses reacting the amine coating with the acetyl chloride of a moiety containing a plurality of halogen atoms, preferably a pentafluoroaryl moiety, to yield a layer which does not interact with proteins. Examples in each of these patents showed good separations, although they all employed high ionic strengths.

Sepaniak disclosed, in *Anal. Chem.* vol. 59, pp. 1466–1470 (1987), the use of trimethylsilyl chloride to give a trimethyl silyl coating which he used in MECC. No examples of analyzed proteins were given. This coating lowers electro-osmotic flow.

All of the above coatings with the exception of the second Swedberg and the Sepaniak papers are hydrophilic coatings which are similar to the types of coatings used on silica gel for high-performance liquid chromatography (HPLC) purposes.

Yeung, in *Anal. Chem.* vol. 62, pp. 2178–2182 (1990), reported a conventional, crosslinked dimethylsilicone coating. This exhibited undesirably low electro-osmotic flow when used in normal CZE, but reasonable flow rates in MECC. Schomburg, above, also reported a silicone coating used for MECC which exhibited increased electro-osmotic flow, but this flow also appears to have been inadequate for good CZE separations.

Tsuda, in *J. Chrom.*, vol. 248, pp. 241–247, (1982), reported reacting a column surface with octadecyl silane, but very little information was given on the performance of the column, and use with biomolecules was not disclosed.

Capillary columns for gas chromatography (GC) may also be treated to deactivate the column surface. These deactivation procedures are intended primarily to keep amines from interacting with the siliceous surface and causing the eluting peaks to tail in gas chromatographic separations; no reason existed heretofore for applying them to CZE columns. The GC column preparation generally employs a 2-step procedure. In the first step the surface is deactivated using one of the following primary methods: 1) high-temperature reaction with a cyclic siloxane; 2) high temperature reaction with a polymeric silicone or disiloxane; 3) high-temperature reaction with a silicone polymer containing Si-H groups; 4) high-temperature reaction with a disilazane; 5) low-temperature reaction with a silyl chloride; and 6) low-temperature reaction with a trialkoxysilane. Following deactivation, the column is coated with a silicone polymer, and this polymer is crosslinked in situ with free-radical initiators such as peroxides or azo compounds.

Each of the deactivation methods for GC columns has been used successfully except the reactions with silyl chloride (5) and trialkoxysilane (6). Although at least some success has been achieved with the trialkoxysilane it is not a preferred method. This is, however, the method disclosed for the GC deactivations described above. The methods involving polymers and cyclic polysiloxanes are preferred, as they are either easier to control or more successfully create an inert surface.

Some of these same approaches are also used to prepare silica-based packings for HPLC. The silyl chloride and trialkoxysilane reactions are most frequently used, but recently the silyl hydride polymer reactions have also been used, as reported by Lee in *Anal. Chem.*, vol. 62, p. 1379 (1990). For HPLC, the goal is not so much to deactivate the surface but to provide a surface functionality for analyte interaction.

An object of the present invention is to deactivate the fused-silica walls of the capillary column to reduce the adsorption of analytes upon the silica during CZE, MECC and other chromatographic separations. Other objects will be apparent from the following description of the invention.

THE INVENTION

We have discovered that certain surface-deactivation techniques, heretofore employed only with gas-chromatographic columns and to achieve different results, may surprisingly be used to deactivate CZE column surfaces without eliminating electro-osmotic flow within the column during CZE and MECC. We have further discovered a method of performing CZE separations and MECC separations which comprises the steps, performed in the order in which they appear, of (a) introducing a buffered solution of analytes into a small-bore, glass, or fused-silica capillary column having a bore diameter smaller than about 100 $\mu$m; having its inner surface covalently bonded to a polymer selected from the group consisting of polymeric silyl hydrides, polymeric siloxanes including cyclic siloxanes, polymeric silazanes and silicone polymers; and having its bore filled with a buffer solution, (b) establishing a high-voltage differential from one end of the column to the other, (c) allowing the analytes to separate within the column and migrate from the column in the buffer solution as it exits the column by electro-osmotic flow, and (d) detecting the analytes in the buffer solution at or near the end of the column.

DETAILED DISCUSSION OF THE INVENTION

The polymers which are useful in the present invention for deactivating the walls of the CZE and MECC columns are polysiloxanes and polysilazanes, including poly(diorganosiloxanes), poly(diorganosilazanes) and poly(organohydrosiloxanes). Examples of the useful polymers include poly(dialkylsiloxanes), poly(alkylsilazanes), poly(arylsiloxanes), poly(arylsilazanes), poly(alkylarylsiloxanes), poly(diarylsiloxanes) and cyclic silazanes and siloxanes, wherein the alkyl groups contain from one to about 24 carbon atoms, more preferably wherein at least one of the alkyl groups contains from about 8 to about 20 carbon atoms, and still more preferably where at least one of the alkyl groups contains from about 12 to about 20 carbon atoms, and the aryl groups are substituted and unsubstituted phenyl, biphenyl or naphthyl. Substituents on the alkyl and aryl groups include hydroxyl, halo, cyano, nitro, amino, mercapto and glycidoxy, and the alkyl groups may contain linking groups such as ether, ester, amide, amine, carbamate and thio. The halo substituents may include fluorine, chlorine and bromine, preferably fluorine. Preferred polymers include poly(n-octylmethylsiloxane), poly(n-octadecylmethylsiloxane), poly(dimethylsiloxane), poly(3,3,3-trifluoropropylmethylsiloxane), poly(diphenylmethylhydrosiloxane), poly(3-cyanopropylphenylsiloxane), poly(bis-3-cyanopropyldimethylsiloxane), poly(dimethylmethylhydrosiloxane), poly(methylphenylsiloxane), poly(diphenylsiloxane) and copolymers thereof.

The polymers useful in the present invention for deactivating the walls of the CZE columns are prepared by methods which are known to those skilled in the art. Examples of methods for preparing these polymers may be found in Noll, *Chemistry and Technology of Silicones*, 2nd edition (1968), published by Academic Press, Orlando, Fla. For instance, cyclic siloxane polymers may be formed by the reaction of dichlorodiorganosilanes or dichloroorganosilanes in the presence of zinc oxide or by the controlled hydrolysis of dichlorodiorganosilanes or dichloroorganosilanes with water. The cyclic polysiloxane ring may then be opened by acid hydrolysis to yield a linear polysiloxane with hydrogen and hydroxyl termination, or by reaction with a trimethylsilanol salt of, for example, potassium or tetraalkylammonium to yield a linear polysiloxane with trimethylsiloxane termination. Organodisiloxanes may be employed to control the molecular weight of the resulting polymers.

The polymers useful in the present invention may be covalently bonded to the walls of the CZE columns by depositing the polysiloxane or polysilazane using static or dynamic coating methods known to those skilled in the art. In the static coating methods the siloxane or silazane is dissolved in a solvent, the column is filled with the resulting solution, one end of the column is closed and the other end is connected to a vacuum source. The solvent is evaporated, leaving a film of the polymer on the column wall.

In the dynamic coating method similar solutions or undiluted polymers are used to partially fill the column, and this solution or polymer is forced through the column with gas pressure or vacuum. This deposits a film of the polymer on the column wall.

In either coating method, following the initial deposition of the polymer film the column is purged with an inert gas, optionally followed by evaporation under vacuum, and the ends of the column are closed, preferably by flame sealing. The column is then heated to a temperature of from about 200° C. to about 450° C. and held at that temperature to allow the polymer to covalently bond with the column wall, preferably from about 10 minutes to about 12 hours. The column is then cooled, the end closures are removed and the column is washed with an organic colvent to remove any unbonded polymer. The resulting column has a deactivated surface coated with a stable, covalently bonded film which is typically 50 nm or less in thickness. Additional, optional treatments of the column include rinsing it with water or a CZE buffer solution to remove any water-soluble residue, and heating it while passing an inert gas through it, to remove any residual volatile materials.

The columns having their walls deactivated according to the present invention are capillary columns having an interior surface of glass or fused silica to which the polymers useful in the present invention are covalently bonded. The maximum internal bore of the columns is limited by the sample heating that results from electrical current flow through the buffer solution within the column; this heating is a function of the cross-sectional area of the column bore and the ionic strength of the buffer solution. The maximum column bore is also limited by diffusion of the sample within the bore; small-bore columns minimize this diffusion. The maximum column bore is preferably about 100 μm, more preferably about 50 μm and still more preferably about 25 μm. At 25 μm and below, the surface-to-volume ratio is superior for CZE and MECC separations. The minimum column bore is limited by the detector limits, and is preferably about 2 μm. The maximum column length is limited by practical limits on analysis time, and is preferably about 5 meters, more preferably about 1 meter, while the minimum column length is limited by the configuration of the particular instrument being used, and is preferably about 5 cm, more preferably about 10 cm.

The conditions for operating the columns having their walls deactivated according to the present invention are readily apparent to those skilled in CZE and MECC separations, and include column and solution temperatures from about 15° C. to about 50° C. and a potential difference across the column of from about 2000 to about 30,000 volts. The buffer solutions useful in the CZE and MECC process of the present invention are also readily apparent to those skilled in CZE and MECC separations, and include aqueous solutions of ionizable salts, including the sodium and potassium salts of phosphoric, boric, acetic and citric acids, and mixtures thereof. The buffer solution may optionally include biological buffer solutions, as for example those prepared from such salts as sodium or potassium chloride, sodium or potassium salts of ethylenediaminetetraacetic acid and halides of tetraalkylammonium salts where the alkyl contains from one to about 5 carbon atoms; surfactants such as cetyltrimethylammonium bromide, Tween ® 20, and the like; organic modifiers including alcohols such as methanol, ethanol and isopropanol, and acetonitrile; and other modifiers such as urea, hydroxyalkylcellulose, ethylene glycol, morpholine and bile salts. Other soluble metal ions may be present for particular separations. Preferred are the sodium and potassium salts of phosphoric, boric, acetic and citric acids, and mixtures thereof. The ionic strength of the buffer solution is preferably about 200 millimolar or less, more preferably from about 10 to about 50 millimolar. The practical lower limit of ionic strength is the concentration that will permit current to flow without causing excessive heating of the solution in the column.

Electro-osmotic flow through a silica column is directly proportional to the number of Si—O— or Si—OH groups available on the column wall. A fused-silica column with no deactivation will produce an electro-osmotic flow of about $9 \times 10^{-4}$ cm$^2$/volt-second. In the CZE and MECC separations of the present invention, this flow is limited to lower values by the effective shielding of silanol groups by the bonded phase, and may approach zero in a column whose walls have been particularly well deactivated according to the present invention.

The analytes that may be separated by CZE or MECC according to the present invention include proteins, biopolymers, peptides, DNA fragments, amino acids and other small molecules, and spans a range from less than 100 Daltons to about 150,000 Daltons, more preferably from about 100 Daltons to about 100,000 Daltons. Examples of such analytes include conalbumin, with a typical size of about 66,000 Daltons, $\beta$-lactoglobulin A and $\beta$-lactoglobulin B, each with a size of about 18,400 Daltons, and myoglobin with a size of about 16,000 Daltons. The method of the present invention is especially suited for proteins and other biological materials which are easily denatured or otherwise degraded by heating, and those which have a particular affinity for the silica surfaces of untreated CZE or MECC columns. The analytes may be present over the concentration range from less than about 5 $\mu$g/ml to about 4 mg/ml, depending upon the limits of the particular detector.

Detection of the analytes during or subsequent to their migration from the column deactivated according to the present invention is a process which is readily performed by those skilled in CZE and MECC separations. Detection methods which will be readily apparent include ultraviolet and visible light absorption, electrochemical detection, fluorescence and mass spectroscopy.

The following examples are intended to illustrate the present invention and not to limit it, except as it is limited in the claims. All ratios and percentages are by weight unless otherwise specified, and all materials are of good commercial quality unless otherwise specified.

Protein mixtures used in the following examples were prepared from lyophilized protein powders obtained from Sigma Chemical Company, St. Louis, Mo. 63178, to contain 1 mg/ml of each protein, and were diluted to final concentration with water. The proteins, with their corresponding pI value, are shown below:

| Protein | pI |
|---|---|
| $\beta$-lactoglobulin A | 5.1 |
| $\beta$-lactoglobulin B | 5.3 |
| Carbonic Anhydrase II | 5.9 |
| Conalbumin | 6.7 |
| Myoglobin | 7.4 |
| Trypsinogen | 9.3 |
| Ribonuclease A | 9.6 |
| Lysozyme | 11.0 |

EXAMPLE 1

This example illustrates deactivation of a capillary column with siloxane polymer.

Fused silica capillary tubing having an outer coating of polyimide, an outer diameter of 350 $\mu$m and an inner diameter (bore) of 50 $\mu$m (Polymicro Technologies, Phoenix, Ariz. 85017), was cut into 10-meter lengths, coiled onto a capillary column frame, and held at 260° C. for 2 hours to remove traces of moisture. A solution of 100 mg poly(n-octylmethylsiloxane) in 50 ml pentane was prepared, and 0.5-1.0 ml of this solution was placed in a pressurizable reservoir. The dried tubing was connected to the reservoir, and the solution was forced through the tubing by pressurizing the reservoir with nitrogen. Nitrogen was then passed through the tubing for 1 hour, after which it was evacuated and held under vacuum for 30 minutes. Both ends of the tubing were then flame-sealed, and the tubing was heated in an oven to 360° C. and held at that temperature for 6 hours. The tubing was then cooled, the seals were cut off, 1-2 ml of pentane was placed in a pressurizable reservoir, and the tubing was connected to the reservoir. The pentane was forced through the tubing at 414 kPa, then the tubing was purged overnight with nitrogen. The tubing was cut into 1-meter lengths and each was marked at 65 cm for a window. The windows were made by dripping fuming sulfuric acid onto the marked area of the tubing to dissolve the imide coating on a 1 to 2-cm segment, wiping off the dissolved coating with a water-moistened cloth and washing the window area thoroughly with water to remove the residual acid. These columns are referred to hereinafter as the "$C_8$" columns.

Using the same procedure, columns were made using poly(dimethysiloxane) (referred to hereinafter as the "dimethyl" columns) and poly(n-octadecylmethylsiloxane) (referred to hereinafter as the "$C_{18}$" columns) in place of the poly(n-octylmethylsiloxane).

EXAMPLE 2

This example illustrates measurement of electro-osmotic flow in the columns useful in the present invention, and comparison of that flow with flow in an untreated column.

The apparatus used was a Model 270A Automated Capillary Electrophoresis System (Applied Biosystems, Inc., Foster City, Calif. 94404), connected to a Spectro-Physics Chromjet Integrator (SpectroPhysics Inc., San Jose, Calif.) and a microcomputer running the MS-DOS operating system and Beckman Gold data-reduction software. Electro-osmotic flow for each column was determined by measuring the mobility of a neutral marker, a 0.01% (vol/vol) aqueous solution of benzyl alcohol, using a 25-millimolar (mM) solution of sodium phosphate adjusted to pH 7.0. Buffers were prepared from mono- and dibasic sodium phosphate. All samples were injected hydrodynamically using vacuum at 17 kPa (absolute) for 1 second, which introduced a 3-nanoliter (nl) sample volume. The voltage differential across the 1-meter columns was 200 v/cm, the length of each column from the injection end to the detector window was 65 cm, and the columns were maintained at a temperature of 30° C. throughout the runs. Analytes were detected photometrically at a wavelength of 200 nm.

Prior to each separation the column was washed for one minute with 0.1M sodium hydroxide solution, followed by a 3-minute rinse with the buffer solution. A conditioning period was observed for each of the columns deactivated according to the present invention, during which the electro-osmotic flow velocity steadily decreased during five runs of 20 to 30-minute duration, after which the flow remained constant. Subsequent to this conditioning period the electro-osmotic flow was determined from the average migration time for the benzyl alcohol neutral marker. Table I, below, shows the results of these determinations for columns deactivated with the three bonded deactivation coatings of the present invention and a fused-silica column that had not been deactivated. In each case the coatings of the present invention reduced the electro-osmotic flow; the $C_{18}$ coating reduced the flow velocity by 37%, the $C_8$ coating reduced it by 43.4% and the dimethyl coating reduced it by 48.8%.

TABLE I

Electro-osmotic Flow in Treated and Untreated Columns

| Column | Electro-osmotic Flow. cm/min. |
|---|---|
| Untreated | 7.67 |
| $C_{18}$ | 4.84 |
| $C_8$ | 4.34 |
| Dimethyl | 3.93 |

EXAMPLE 3

This example illustrates the electrophoretic mobility of the benzyl alcohol neutral marker in the $C_{18}$ and dimethyl columns of the present invention, and in an untreated silica column, as a function of the pH of the buffer solution.

Using the procedure described in Example 2, but with 25 mM sodium phosphate buffer solutions adjusted to pH values between 3 and 10 and constant ionic strength, samples of a 0.01% (vol/vol) aqueous solution of benzyl alcohol were injected into the $C_{18}$, dimethyl and untreated, fused-silica columns, and the electrophoretic mobility of the samples in the columns, in units of $10^{-4}$ cm$^2$/V, was determined. The results of these determinations is shown in Table II, following Example 4, below.

EXAMPLE 4

This example illustrates the electrophoretic mobility of the benzyl alcohol neutral marker in the $C_8$ column of the present invention, and in an untreated silica column, as a function of the pH of the buffer solution.

The electrophoretic mobility of samples of the benzyl alcohol neutral marker were determined for $C_8$ columns of 50-$\mu$m inside diameter and 48-cm length, with a length to the detector of 37 cm, compared directly with untreated, fused-silica columns of the same dimensions, over a pH range from 3 to 9.5. The aqueous buffer solutions were prepared as 10 mM sodium phosphate/6 mM sodium borate solutions and adjusted to the indicated pH and a constant ionic strength. A manually operated capillary electrophoresis system was used which included a Hippotronics Model 840A power supply (Hipotronics, Inc., Brewster, N.Y. 10509) for generating a potential difference of 20 kilovolts and a modified Laboratory Data Control Model UV III (Hipotronics, Inc., Brewster, N.Y. 10509) adsorbance detector operating at a wavelength of 229 nm. The columns were at room temperature (approximately 23° C.) throughout the runs. The samples of 0.01% (vol/vol) aqueous benzyl alcohol solution were injected hydrostatically by inserting the injection end of the columns in the sample solution and raising the injection end 10 cm above the elution end of the column. Each column was flushed between injections for five minutes with buffer solution. The results of these determinations are shown in Table II, below.

TABLE II

Electrophoretic Mobility of Neutral Marker in Treated and Untreated Columns

| | Column | | | |
|---|---|---|---|---|
| pH | Untreated | $C_{18}$ | $C_8$ | Dimethyl |
| 3 | 2.67 | 1.90 | 2.33 | No data |
| 4 | 5.96 | 2.53 | 2.51 | No data |
| 5 | 7.21 | 2.93 | 2.51 | 2.79 |

TABLE II-continued

Electrophoretic Mobility of Neutral Marker in Treated and Untreated Columns

| | Column | | | |
|---|---|---|---|---|
| pH | Untreated | $C_{18}$ | $C_8$ | Dimethyl |
| 6 | 7.84 | 2.85 | 2.38 | 3.15 |
| 7 | 8.40 | 3.47 | 3.10 | 3.93 |
| 8 | 8.40 | 3.84 | 3.00 | 4.32 |
| 9 | 8.28 | 3.88 | 3.16 | 4.19 |
| 10 | 8.34 | 3.85 | 3.18 | 4.02 |

As may be seen from the results in Table II, the change in electrophoretic mobility with changing pH is greatly reduced in the columns of the present invention, compared with the untreated, fused-silica columns.

EXAMPLE 5

This example illustrates migration of conalbumin using the method of the present invention, compared with conalbumin migration on an untreated, fused-silica column.

The separation of this example was performed using the equipment and procedure of Example 4, above, except that the reference column was an untreated, fused-silica column with an inside diameter of 50 $\mu$m and a length of 75 cm, and the treated column of the present invention was a $C_{18}$ column with an inside diameter of 50 $\mu$m and a length of 50 cm. The buffer was aqueous, 10 mM sodium phosphate/6 mM sodium borate with its pH adjusted as shown in Table IV, below. The sample was a 1 mg/ml conalbumin solution. The results of these separations are shown below in Table III.

TABLE III

| | | Conalbumin Migration | |
|---|---|---|---|
| Column | pH | Migration Time, min. | Comments |
| Untreated | 8.3 | 13 | Serious tailing |
| Untreated | 10.1 | 15 | Sharp peak, some sample absorption |
| $C_{18}$ | 8.0 | 8 | Sharp peak |

EXAMPLE 6

This example illustrates separation of proteins according to the method of the present invention, compared with results from an untreated, fused-silica column.

A protein sample was prepared containing four proteins: myoglobin, conalbumin, $\beta$-lactoglobulin A and $\beta$-lactoglobulin B. Using the procedure, apparatus and $C_8$ column of Example 4, this sample was separated using aqueous buffer solutions of 10 mM sodium phosphate/6 mM sodium borate adjusted to pH 6.2, pH 7.2 and pH 9.2, respectively. The results of these separations are shown in Table IV, below.

TABLE IV

Protein Separations Using $C_8$ Column at Different pH Values

| | Migration Time of Protein, minutes | | | |
|---|---|---|---|---|
| pH | Myoglobin | Conalbumin | $\beta$-lactoglobulin A | $\beta$-lactoglobulin B |
| 9.2 | 8.5[1] | 8.5[1] | 19.0 | 21.8 |
| 7.2 | 8.0[2] | 8.1[2] | 16.8 | 19.0 |

TABLE IV-continued

Protein Separations Using C8 Column at Different pH Values

| | | Migration Time of Protein, minutes | | |
|---|---|---|---|---|
| pH | Myoglobin | Conalbumin | β-lactoglobulin A | β-lactoglobulin B |
| 6.2 | 7.7[3] | 8.1[3] | 16.8[4] | 18.8 |

[1] Peaks unresolved, accurate measurement impossible.
[2] Peaks partially resolved, accurate measurement difficult.
[3] Peaks fully resolved to baseline.
[4] Partial resolution of a fifth peak, hidden at higher pH.

EXAMPLE 7

This example illustrates separation of proteins at various pH levels according to the method of the present invention, using the dimethyl column described in Example 1 and a comparison column of untreated, fused silica.

Samples containing the four proteins used in Example 6 were injected hydrodynamically into 50-μm × 1-meter dimethyl and untreated, fused-silica columns using the procedure and automated equipment of Example 2. The 10 mM sodium phosphate/6 mM sodium borate buffer solution was adjusted to the pH values indicated in Table V, below, and the separations were conducted with a potential difference of 20 kV across the column, and at a temperature of 30° C.

TABLE V

Protein Separations Using Dimethyl and Untreated Columns at Different pH Values

| Column | pH | Myoglobin | Conalbumin | β-Lactoglobulin B | β-Lactoglobulin A |
|---|---|---|---|---|---|
| Dimethyl | 7.0 | 20.24 | 29.13 | 39.31 | 43.65 |
| " | 7.5 | 20.96 | 23.61 | 41.08 | 45.90 |
| " | 8.0 | 21.18 | 22.22 | 38.68 | 42.53 |
| Untreated | 6.0 | No separation; essentially complete adsorption of sample proteins | | | |
| Untreated | 7.0 | Broad, ill-defined peak at 14 minutes | | | |
| Untreated | 8.0 | 8.59 | 10.90 | 11.22 | 11.64 |
| Untreated | 9.0 | 8.83 | 9.13 | 10.89 | 11.50[1] |

[1] A fifth peak, hidden at lower pH, also appears.

I claim:

1. A method of performing capillary zone electrophoresis separations and micellar electrokinetic capillary chromatography separations which comprises the steps, performed in the order in which they appear, of
   (a) introducing a buffered solution of analytes into a small-bore, glass or fused-silica capillary column having a bore diameter smaller than about 100 μm; having its inner surface covalently bonded to a polymer having a silicon backbone selected from the group consisting of polymeric silyl hydrides, polymeric siloxanes, polymeric cyclic siloxanes, polymeric silazanes and silicone polymers; and having its bore filled with a buffer solution,
   (b) establishing a high-voltage differential from one end of the column to the other,
   (c) allowing the analytes to separate within the column and migrate from the column in the buffer solution as it exits the column by electro-osmotic flow, and
   (d) detecting the analytes in the buffer solution at or near the end of the column.
2. The method of claim 1 wherein the polymer is a polymeric siloxane.
3. The method of claim 2 wherein the polymeric siloxane is a poly(dialkylsiloxane).
4. The method of claim 2 wherein the polymeric siloxane is a poly(arylsiloxane).
5. The method of claim 2 wherein the polymeric siloxane is a poly(alkylarylsiloxane).
6. The method of claim 2 wherein the polymeric siloxane is a poly(diarylsiloxane).
7. The method of claim 1 wherein the polymer is a polymeric silazane.
8. The method of claim 7 wherein the polymeric silazane is a poly(alkylsilazane).
9. The method of claim 7 wherein the polymeric silazane is a poly(arylsilazane).
10. The method of claim 2 wherein the polymeric siloxane is a polymeric cyclic siloxane.
11. The method of claim 7 wherein the polymeric silazane is a polymeric cyclic silazane.
12. The method of claim 3 wherein the polymeric siloxane is a poly(n-octylmethylsiloxane)
13. The method of claim 3 wherein the polymeric siloxane is a poly(n-octadecylmethylsiloxane).

* * * * *